United States Patent
Laffranchi et al.

(10) Patent No.: US 11,160,714 B2
(45) Date of Patent: Nov. 2, 2021

(54) FOOT FOR A ROBOTIC EXOSKELETON FOR ASSISTED WALKING OF PERSONS SUFFERING FROM LOCOMOTOR DISORDERS

(71) Applicants: FONDAZIONE ISTITUTO ITALIANO DI TECNOLOGIA, Genoa (IT); ISTITUTO NAZIONALE PER L'ASSICURAZIONE CONTRO GLI INFORTUNI SUL LAVORO, Rome (IT)

(72) Inventors: Matteo Laffranchi, Genoa (IT); Stefano D'Angella, Albisola Superiore (IT); Paolo Uboldi, Sant'Olcese (IT); Jody Alessandro Saglia, Genoa (IT); Carlo Sanfilippo, Genoa (IT)

(73) Assignee: FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 156 days.

(21) Appl. No.: 15/745,246

(22) PCT Filed: Jul. 14, 2016

(86) PCT No.: PCT/IB2016/054195
§ 371 (c)(1),
(2) Date: Jan. 16, 2018

(87) PCT Pub. No.: WO2017/009795
PCT Pub. Date: Jan. 19, 2017

(65) Prior Publication Data
US 2019/0000708 A1 Jan. 3, 2019

(30) Foreign Application Priority Data
Jul. 15, 2015 (IT) .................. 102015000034470

(51) Int. Cl.
*A61H 3/00* (2006.01)
*B25J 13/08* (2006.01)
(Continued)

(52) U.S. Cl.
CPC ............. *A61H 3/00* (2013.01); *A61F 5/0127* (2013.01); *B25J 9/0006* (2013.01); *B25J 13/085* (2013.01);
(Continued)

(58) Field of Classification Search
CPC ................ A61H 3/00; A61H 2201/165; A61H 2201/1654; A61H 2201/1688; A61H 2201/1697
See application file for complete search history.

(56) References Cited

U.S. PATENT DOCUMENTS 2,446,042 A * 7/1948 Mario ........................ A61F 2/66
623/26
2,478,664 A * 8/1949 Morrow .................. A43B 3/128
36/31
(Continued)

FOREIGN PATENT DOCUMENTS

CN 103057620 A 4/2013

*Primary Examiner* — LaToya M Louis
(74) *Attorney, Agent, or Firm* — Arent Fox LLP; Michael Fainberg (57) ABSTRACT

A foot for a robotic exoskeleton includes three rigid foot segments, namely a middle foot segment arranged to be connected to a leg of the robotic exoskeleton, a front foot segment elastically connected to the front end of the middle foot segment by a first set of leaf springs and a rear foot segment elastically connected to the rear end of the middle foot segment by a second set of leaf springs. The foot has laces for fastening the foot to a person's shoe. In the condition where the front foot segment and the rear foot segment are both in contact with the ground, and no load is applied onto the foot, the middle foot segment is not in (Continued)

contact with the ground, but is elastically suspended by the first and second sets of springs.

10 Claims, 6 Drawing Sheets

(51) Int. Cl.
*A61F 5/01* (2006.01)
*B25J 9/00* (2006.01)

(52) U.S. Cl.
CPC ..... *B25J 13/088* (2013.01); *A61F 2005/0155* (2013.01); *A61H 2201/0107* (2013.01); *A61H 2201/0165* (2013.01); *A61H 2201/0192* (2013.01); *A61H 2201/164* (2013.01); *A61H 2201/165* (2013.01)

(56) References Cited

U.S. PATENT DOCUMENTS

| | | | | |
|---|---|---|---|---|
| 2,522,515 | A * | 9/1950 | Hill | A43B 13/141 36/104 |
| 5,376,141 | A * | 12/1994 | Phillips | A61F 2/66 623/38 |
| 6,197,068 | B1 | 3/2001 | Christensen | |
| 7,284,341 | B2 * | 10/2007 | Moseley | A43B 3/0026 36/103 |
| 8,092,550 | B2 * | 1/2012 | McCarvill | A61F 2/66 623/55 |
| 8,961,618 | B2 * | 2/2015 | Lecomte | A61F 2/66 623/55 |
| 9,011,554 | B2 * | 4/2015 | Rubie | A61F 2/66 623/55 |
| 2005/0049721 | A1 | 3/2005 | Sulprizio | |
| 2008/0281436 | A1 | 11/2008 | Townsend | |
| 2010/0083541 | A1 * | 4/2010 | Baucom | A43C 15/168 36/25 R |
| 2010/0236096 | A1 * | 9/2010 | Pauk | A43B 13/183 36/28 |
| 2013/0024008 | A1 * | 1/2013 | Treger | A61F 2/66 623/55 |
| 2015/0059207 | A1 * | 3/2015 | Karlsson | A45B 9/04 36/61 |
| 2016/0058124 | A1 * | 3/2016 | Lucas | A43B 13/14 36/28 |

* cited by examiner

FOOT FOR A ROBOTIC EXOSKELETON FOR ASSISTED WALKING OF PERSONS SUFFERING FROM LOCOMOTOR DISORDERS

CROSS-REFERENCE TO RELATED APPLICATIONS

This application is the U.S. National Stage Application of International Patent Application No. PCT/IB2016/054195, filed on Jul. 14, 2016, which claims priority to Italian Patent Application No. 102015000034470, filed on Jul. 15, 2015, the contents of each of which is incorporated herein by reference in its entirety.

BACKGROUND

The present invention relates to a foot for a robotic exoskeleton for assisted walking of persons suffering from locomotor disorders.

According to the Online Dictionary of Prosthetics and Orthotics available on the website of ISPO (International Society for Prosthetics and Orthotics) at http://www.ispo.ca/lexicon/, an exoskeleton is defined as a type of prosthetic construction whose structural components are located peripherally to the existing limb, whereas a limb prosthesis is defined as a device used to replace, wholly or in part, a missing or deficient limb segment.

That being stated, the present invention does not relate to a foot prosthesis, i.e. a device designed to replace the foot of a patient, but to a foot for a robotic exoskeleton, i.e. a device designed to be "worn" by the foot of the patient to assist the patient during walking.

The feet for robotic exoskeletons for assisted walking of persons suffering from locomotor disorders that are currently available on the market have a rigid structure which makes it difficult for the robotic exoskeleton to replicate the natural gait of a person.

SUMMARY

It is therefore an object of the present invention to provide a foot for a robotic exoskeleton for assisted walking of persons suffering from locomotor disorders which is not affected by the above-mentioned disadvantage of the prior art. More specifically, the present invention aims at providing a foot for a robotic exoskeleton for assisted walking of persons suffering from locomotor disorders which is able to efficiently absorb the shocks with the ground, in particular at the beginning of the stance phase, to deform at the end of the stance phase (i.e. when the heel first and then also the toes leave the ground), as well as to measure the forces exchanged by the foot with the ground.

A further object of the present invention is to provide a foot for a robotic exoskeleton for assisted walking of persons suffering from locomotor disorders which is structurally simple and has a reduced number of components.

These and other objects are fully achieved according to the present invention by virtue of a foot for a robotic exoskeleton for assisted walking of persons suffering from locomotor disorders having the features set forth in independent claim 1.

Advantageous embodiments of the present invention are defined in the dependent claims, whose subject-matter is to be intended as forming an integral and complementary part of the following description.

In short, the invention is based on the concept of providing a foot for a robotic exoskeleton for assisted walking of persons suffering from locomotor disorders which comprises three rigid foot segments, namely a middle foot segment arranged to be connected to a leg of the robotic exoskeleton, a front foot segment elastically connected to the front end of the middle foot segment by means of a first set of leaf springs, and a rear foot segment elastically connected to the rear end of the middle foot segment by means of a second set of leaf springs. By virtue of such a configuration, the three foot segments are able to rotate relative to each other both about a transverse axis and about the longitudinal axis of the foot, thereby allowing the foot to absorb the irregularities of the ground in a very efficient manner.

Preferably, in the condition where the foot is wholly resting on the ground, i.e. in the condition where the front foot segment and the rear foot segment are both in contact with the ground, and there is no load acting on the foot, the middle foot segment is not in contact with the ground, but is elastically suspended by means of the first and second sets of springs. Since the leg of the robotic exoskeleton is connected to the foot at the middle foot segment and since the middle foot segment is elastically suspended between the front and rear foot segments, the foot of the invention has a greater ability to absorb the shocks, in particular during the stance phase, than the prior art.

Preferably, the foot further comprises force measuring means for providing measurements indicative of the forces applied onto the foot. These measuring means advantageously comprise strain gauges that are positioned on the leaf springs and therefore allow to detect not only the forces/torques applied onto the foot, but also the angles of rotation between each pair of adjacent foot segments.

According to an embodiment, the leaf springs are constrained to deflect along a suitably shaped curved profile in such a manner that the active length of the springs decreases, and therefore stiffness of the springs increases, as the force exchanged between the front (or rear) foot segment and the middle foot segment increases. This allows to prevent the various foot segments from reaching end-of-travel positions, for example the middle foot segment from coming into contact with the ground, as a result of the normal forces exchanged between foot and ground during walking.

BRIEF DESCRIPTION OF THE DRAWINGS

Further features and advantages of the present invention will become apparent from the following detailed description, given purely by way of non-limiting example with reference to the appended drawings, where.

DETAILED DESCRIPTION

Figure 8:
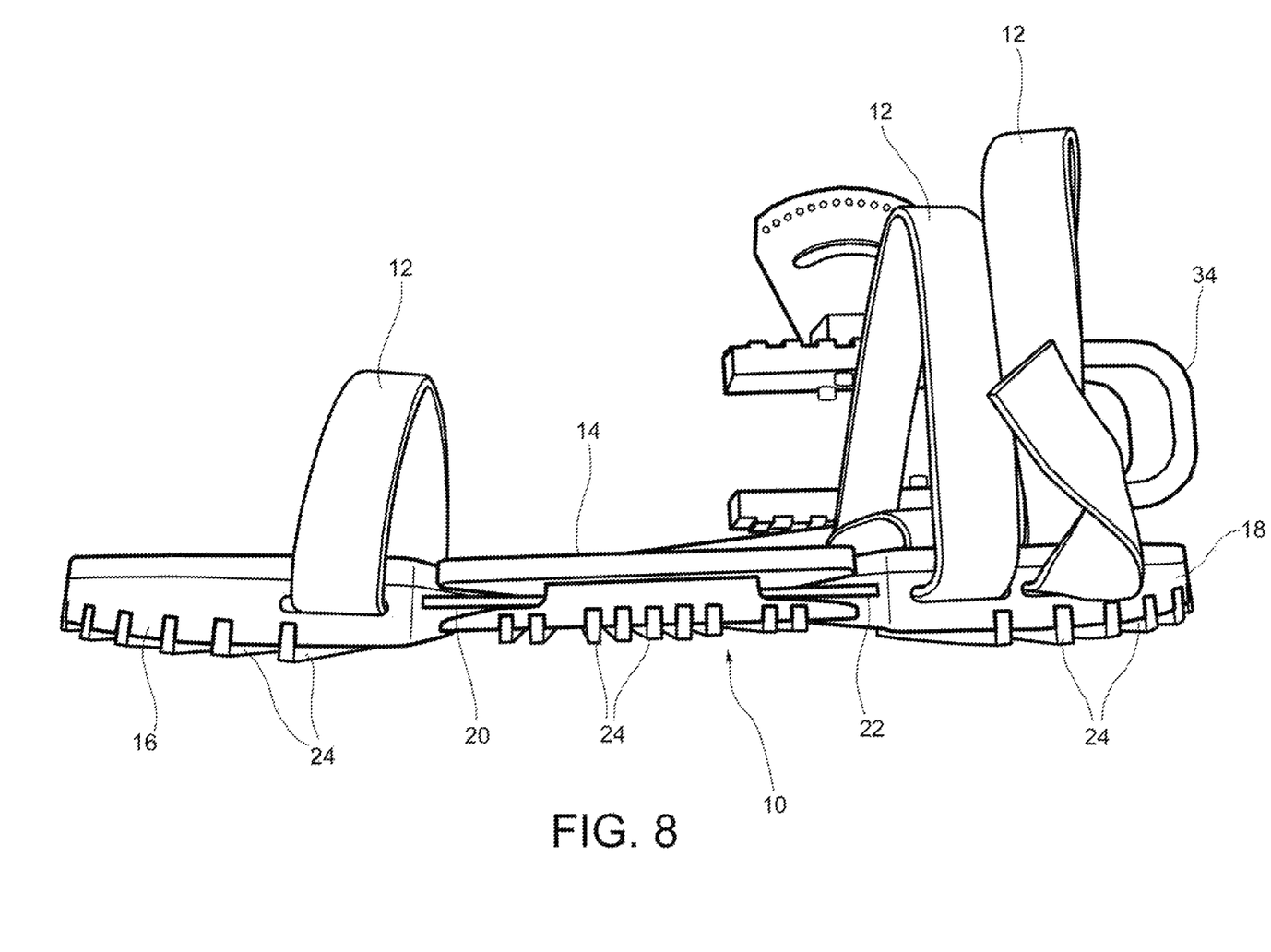
FIG. 8 is a side view of a foot for a robotic exoskeleton for assisted walking of persons suffering from locomotor disorders provided with laces for fastening the foot to a shoe of a patient.

With reference first to FIGS. 1 to 5, as well as to FIG. 8, a foot for a robotic exoskeleton for assisted walking of persons suffering from locomotor disorders according to an embodiment of the present invention is generally indicated 10. The foot 10 is mainly intended for use as a sort of sole on which the patient may rest with his foot, wearing a shoe. To this end, the foot 10 is advantageously provided with a number of laces 12 for fastening the foot 10 to the shoe of the patient, as shown in FIG. 8.

The foot 10 basically comprises three rigid foot segments, namely a middle foot segment 14 arranged to be connected to a leg (not shown, but of per-se-known type) of the robotic exoskeleton, a front foot segment 16 elastically connected to the front end of the middle foot segment 14 by means of a first set of leaf springs and a rear foot segment 18 elastically connected to the rear end of the middle foot segment 14 by means of a second set of leaf springs.

Figure 5:
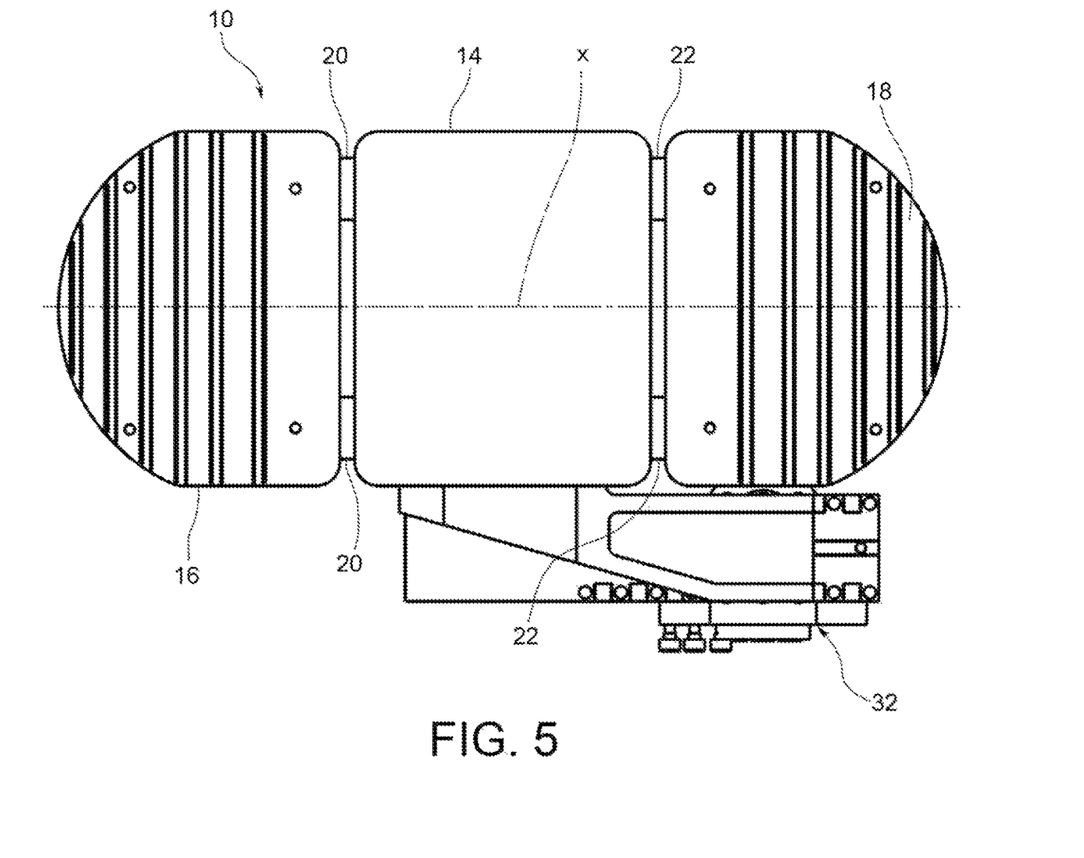
FIG. 5 is a plan view from below of the foot of FIGS. 1 and 2.

As shown in FIG. 5, in the proposed embodiment the first set of leaf springs comprises a pair of leaf springs 20 arranged on opposite sides of a longitudinal axis x of the foot 10, symmetrically to this axis. Likewise, the second set of leaf springs comprises a pair of leaf springs 22 arranged on opposite sides of the longitudinal axis x, symmetrically to this axis. The first and/or second set of leaf springs might comprise a number of leaf springs different from the one proposed here. Moreover, the term "leaf spring" is used here to refer not necessarily to a single leaf spring, but more generally to a pack of leaf springs, whose number may be suitably chosen by the designer based on the stiffness requirements, which may for example depend on the intended use of the foot or on the weight of the patient. Different stiffness values may also be set, both between the leaf springs 20 (front springs) and the leaf springs 22 (rear springs), and between the two springs (the one placed on the left side and the one placed on the right side) of the same set of springs 20 or 22, for example to adapt the behaviour of the foot to the preferences of the patient or to help to correct possible posture errors of the patient.

By virtue of the elastic connection through the leaf springs 20 the front foot segment 16 is able to rotate relative to the middle foot segment 14 both in the sagittal plane (i.e. the vertical plane passing through the longitudinal axis x), that is to say, about an axis of rotation directed transversely to the longitudinal axis x, and in the front plane (i.e. the vertical plane perpendicular to the longitudinal axis x), that is to say, about the longitudinal axis x. Likewise, by virtue of the elastic connection through the leaf springs 22 the rear foot segment 18 is able to rotate relative to the middle foot segment 14 both in the sagittal plane and in the front plane. A foot for a robotic exoskeleton according to the invention is thus able to adapt very efficiently to the ground, suitably deforming to absorb possible irregularities of the ground. Moreover, an exoskeleton provided with a foot according to the invention is able to replicate the gait of a person more accurately than the prior art, thanks to the ability of the three foot segments to move relative to each other.

Figure 6:
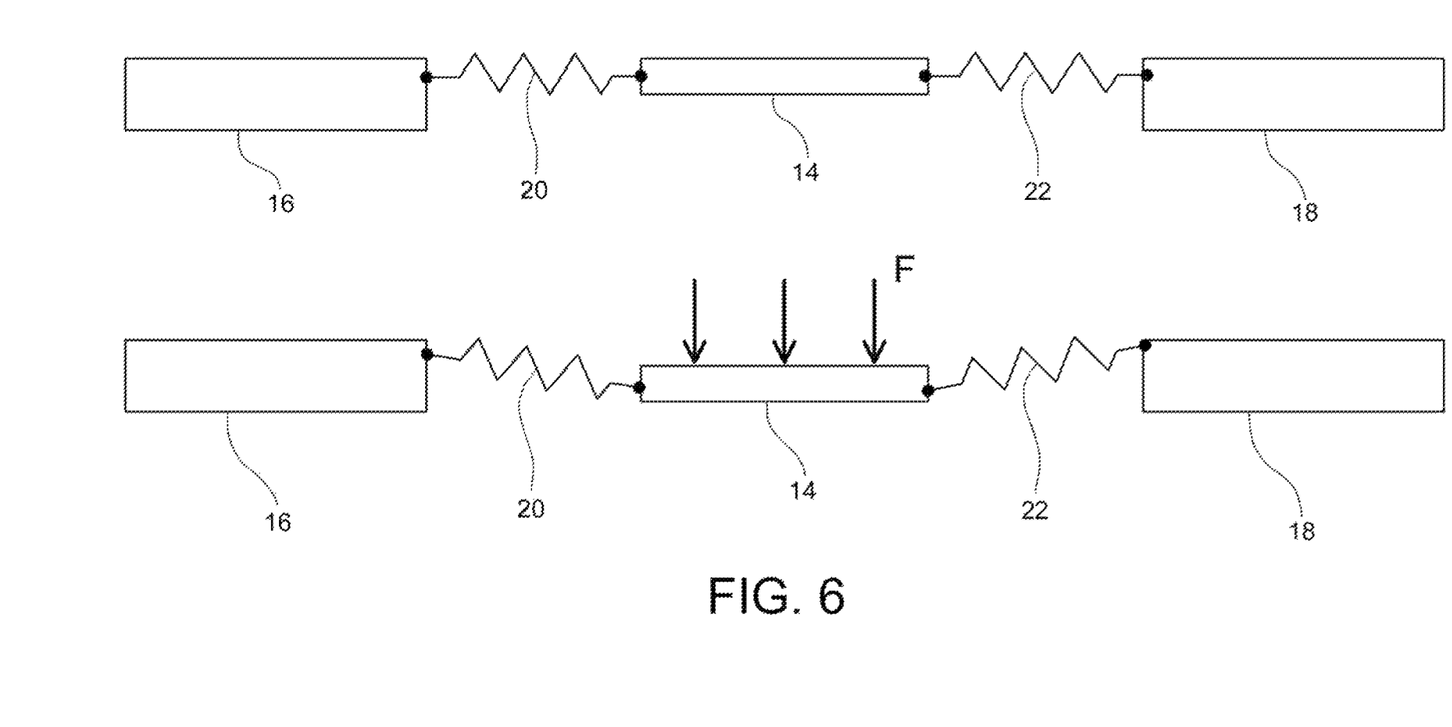
FIG. 6 schematically shows the principle of operation of the foot according to the invention.

As shown both in the schematic drawing of FIG. 6 and in the side view of FIG. 8, the foot 10 is configured in such a manner that in the condition where the foot is wholly resting on the ground, i.e. in the condition where the front foot segment 16 and the rear foot segment 18 are both in contact with the ground, the middle foot segment 14 is not instead in contact with the ground, but elastically suspended by means of the two pairs of leaf springs 20 and 22. Preferably, the leaf springs 20 and 22 are so configured as to keep the middle foot segment 14 at a distance from the ground even when this foot segment is subject to forces F during the stance phase. On the one hand this makes the patient perceive a greater "softness" of operation of the robotic exoskeleton and on the other helps to improve the ability of the foot to adapt to the ground shape.

The three foot segments 14, 16 and 18 are preferably provided with studs 24 of elastomeric material acting as shock-absorbing elements for absorbing the shocks of the foot 10 with the ground. The studs 24 are partially received in transverse grooves 26 formed on the bottom face of each of the three foot segments 14, 16 and 18 so as to project downwards from this face, as shown in FIG. 8.

The foot 10 is also preferably provided with measuring means for providing measurements indicative of the forces applied onto the foot. According to an embodiment, these measuring means are formed by strain gauges (not shown, but of per-se-known type) which are positioned on the leaf springs 20 and 22 (or, more generally, on at least one of said first and second sets of leaf springs). The use of strain gauges on the leaf springs allows to detect not only the forces applied onto the foot, but also the angles of rotation between each pair of adjacent foot segments.

Figure 4:
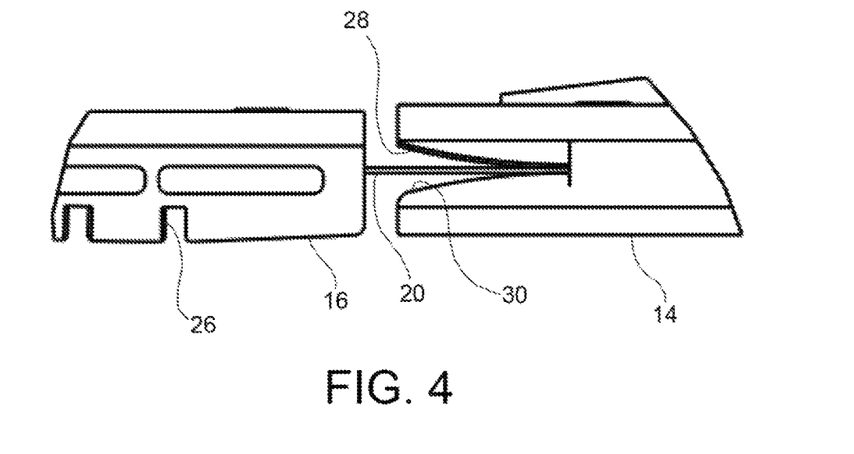
FIG. 4 is a view on an enlarged scale of detail A of FIG. 3.
Figure 7:
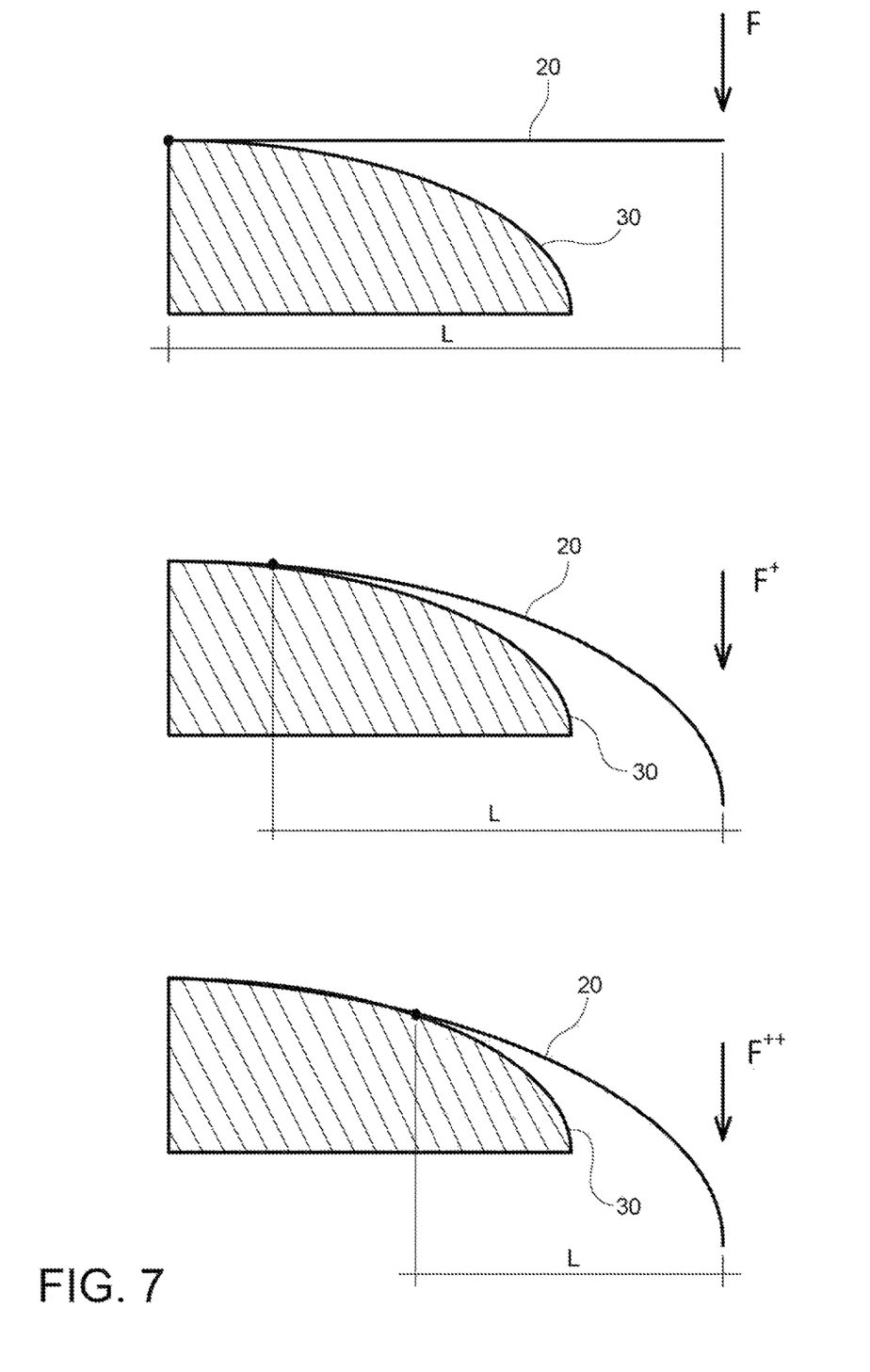
FIG. 7 shows the deflection of one of the leaf springs of the foot of FIGS. 1 and 2 for three different values of the force acting onto the spring.

With reference now in particular to FIGS. 4 and 7, according to a preferred aspect of the present invention the first and second sets of leaf springs 20 and 22 are constrained to deflect along a curved profile suitably configured in such a manner that the active length of the springs decreases, and therefore the stiffness of the springs increases, as the angle of rotation between the two foot segments connected by means of these springs (front foot segment 16 and middle foot segment 14 or rear foot segment 18 and middle foot segment 14) increases. An upper abutment surface 28 and a lower abutment surface 30 are therefore provided on vertically opposite sides of each of the leaf springs 20, 22, preferably on the middle foot segment 14, which surfaces have respective curved profiles, preferably symmetrically arranged with respect to the plane passing through the spring in the undeformed condition. As shown in FIG. 7, as the force acting onto the spring 20, 22 increases, and therefore the deflection of the spring increases, the portion of spring in contact with the abutment surface (in this case the lower abutment surface 30) also increases, and therefore the active length (indicated L in FIG. 7) of the spring decreases, which results in an increase in the stiffness of the same spring. This allows to avoid that the foot segments reach end-of-travel positions, for example that the middle foot segment 14 comes into contact with the ground, as a result of the normal forces exchanged between foot and ground during walking.

Figure 1:
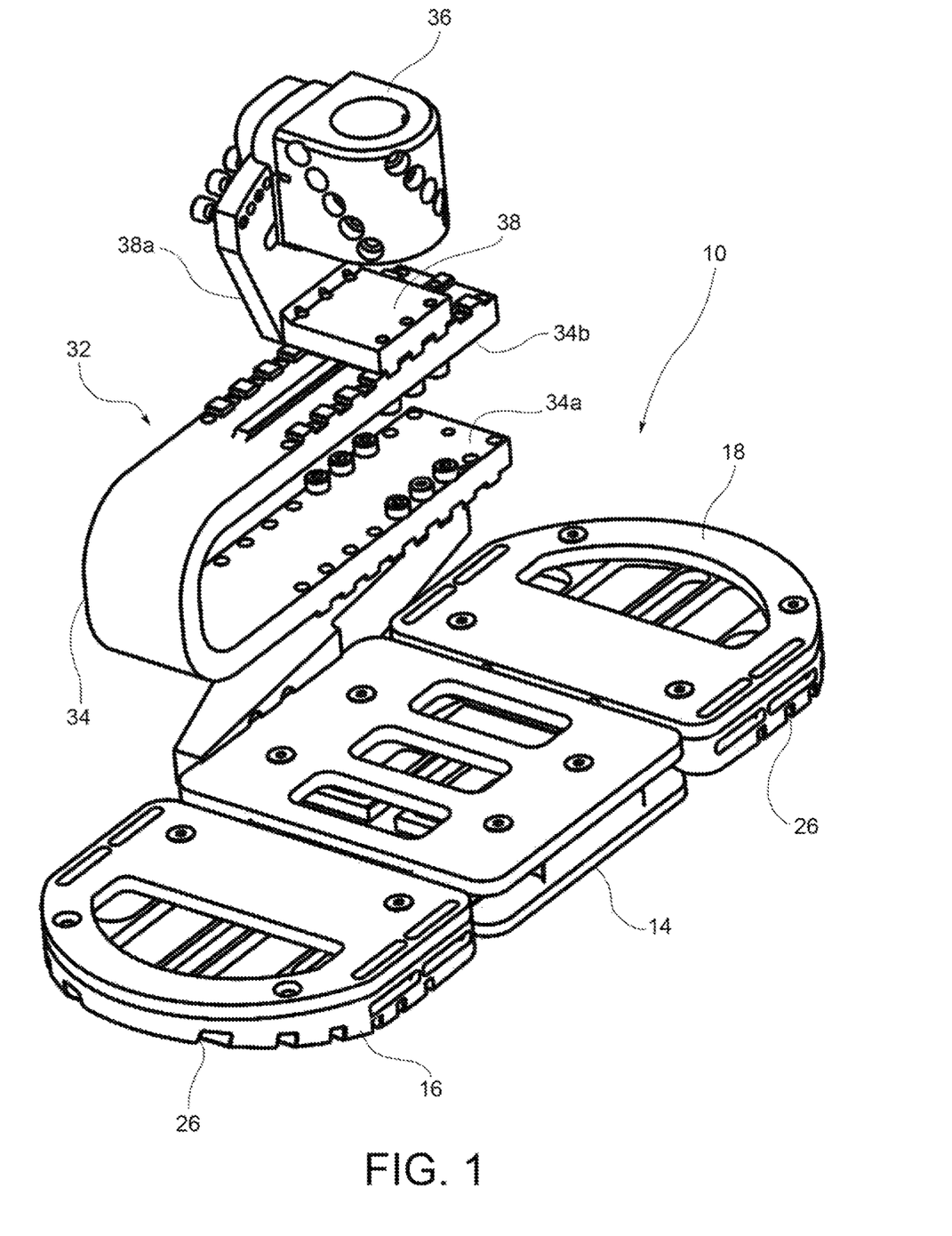
FIGS. 1 and 2 are perspective views, from two different points of view, of a foot for a robotic exoskeleton for assisted walking of persons suffering from locomotor disorders according to an embodiment of the present invention.
Figures 2, 3:
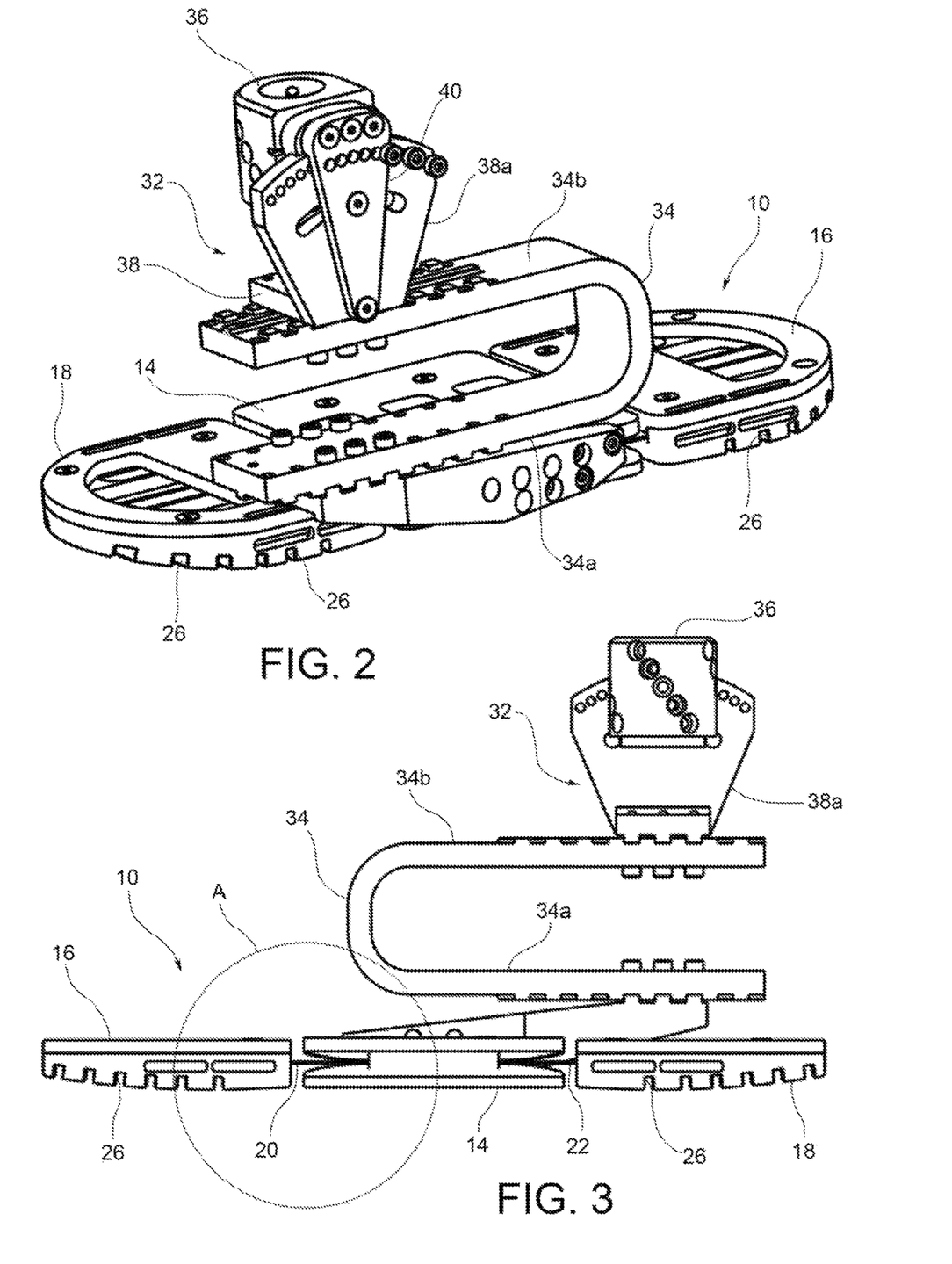
FIG. 3 is a side view of the foot of FIGS. 1 and 2.

As explained above, the leg (not shown) of the robotic exoskeleton is connected to the foot 10 at the middle foot segment 14, in particular by means of a joint 32 simulating the ankle joint. With reference in particular to FIGS. 1 to 3, in the proposed embodiment the joint 32 comprises a C-shaped spring element 34 extending in the sagittal plane. The lower limb of the spring 34, indicated 34a, is rigidly connected to the middle foot segment 14, while the upper limb, indicated 34b, is connected to a connection member 36 to which the bottom end of the leg is intended to be attached. By virtue of its flexibility, the spring 34 allows to replicate the flexion and extension movements of the ankle. The joint 32 might also comprise additional spring devices, for example a spring device arranged to replicate the inversion and eversion movements of the ankle.

Preferably, the joint 32 further comprises an adjustment device for adjusting the angular position, in the sagittal plane, of the connection member 36 relative to the upper limb 34b of the spring element 34, and therefore the angular position of the leg of the robotic exoskeleton relative to the middle foot segment 14, in the undeformed condition of the spring element 34, in order to adapt the exoskeleton to the personal preferences of the patient or to correct possible unbalances in the sagittal plane due to posture defects of the patient. According to the proposed embodiment, the adjustment device comprises a bracket element 38 which is rigidly connected to the upper limb 34b of the spring element 34 and a movable element 40 which is rigidly connected to the connection member 36 and is attachable to the bracket element in a plurality of different angular positions in the sagittal plane. More specifically, the bracket element 38 comprises a vertical wall 38a extending in the sagittal plane and the movable element 40 is hinged to the vertical wall 38a of the bracket element so that it can be rotated relative to the latter in the sagittal plane until it reaches the desired orientation and then fixed in this position, for example by means of screws.

In view of the above description the advantages offered by a foot for a robotic exoskeleton according to the present invention are evident.

First of all, the foot is able to adapt to the shape of the ground, and therefore to absorb possible irregularities of the same, by virtue of the possibility of relative rotation between the foot segments both in the sagittal plane and about the longitudinal axis of the foot.

Secondly, the foot is able to efficiently absorb the shocks with the ground, by virtue of the middle foot segment being elastically suspended between the front and rear foot segments.

Moreover, since strain gauges may be applied directly onto the leaf springs the invention provides a simple, yet very efficient, solution to the problem of detecting both the forces/torques exerted onto the foot and the angles of rotation between each pair of adjacent foot segments.

Naturally, the principle of the invention remaining unchanged, the embodiments and the constructional details may vary widely from those described and illustrated purely by way of non-limiting example, without thereby departing from the scope of the invention as defined in the appended claims.

The invention claimed is:

1. A foot for a robotic exoskeleton for assisted walking of persons suffering from locomotor disorders, the foot comprising:
    three rigid foot segments, including a middle foot segment arranged to be connected to a leg of the robotic exoskeleton, a front foot segment and a rear foot segment, and laces for fastening the foot to a person's shoe,
    wherein each of the three rigid foot segments is configured to simultaneously contact the ground when load is applied onto the foot,
    wherein the front foot segment is elastically connected to a front end of the middle foot segment by means of a first set of leaf springs,
    wherein the rear foot segment is elastically connected to a rear end of the middle foot segment by means of a second set of leaf springs, and
    wherein in a condition where the front foot segment and the rear foot segment are both in contact with the ground and no load is applied onto the foot, the middle foot segment is not in contact with the ground, but is elastically suspended by means of the first and second sets of springs.

2. The foot of claim 1, wherein the first set of leaf springs comprises a pair of leaf springs arranged on opposite sides of a longitudinal axis of the foot.

3. The foot of claim 2, wherein the second set of leaf springs comprises a pair of leaf springs arranged on opposite sides of the longitudinal axis of the foot.

4. The foot of claim 1, wherein the second set of leaf springs comprises a pair of leaf springs arranged on opposite sides of a longitudinal axis of the foot.

5. The foot of claim 1, further comprising strain gauges located on at least one of said first and second sets of leaf springs.

6. The foot of claim 1, wherein the first and second sets of leaf springs are constrained to deflect along a curved profile suitably configured in such a manner that an active length of the first and second sets of leaf springs decreases, and therefore stiffness of these springs increases, as the force exchanged between the front foot segment, or the rear foot segment, and the middle foot segment increases.

7. The foot of claim 6, wherein the middle foot segment has, both for the first set of leaf springs and for the second set of leaf springs, a respective upper abutment surface and a respective lower abutment surface each having said curved profile, the curved profile of the upper abutment surface being arranged symmetrically to the curved profile of the respective lower abutment surface with respect to a plane passing through the respective set of leaf springs in an undeformed condition.

8. The foot of claim 1, further comprising a joint for connection of the leg of the robotic exoskeleton to the middle foot segment, said joint being configured to allow relative rotation between the leg and the middle foot segment at least in the sagittal plane of the foot.

9. The foot of claim 8, wherein said joint comprises a C-shaped spring element extending in the sagittal plane of the foot, with a lower limb rigidly connected to the middle foot segment and with an upper limb connected to a connection member to which the bottom end of the leg is intended to be connected.

10. The foot of claim 9, wherein said joint further comprises an adjustment device for adjusting the angular position, in the sagittal plane, of the connection member relative to the upper limb of the spring element.

* * * * *

UNITED STATES PATENT AND TRADEMARK OFFICE
CERTIFICATE OF CORRECTION

PATENT NO. : 11,160,714 B2
APPLICATION NO. : 15/745246
DATED : November 2, 2021
INVENTOR(S) : Matteo Laffranchi et al.

Page 1 of 1

It is certified that error appears in the above-identified patent and that said Letters Patent is hereby corrected as shown below:

On the Title Page

(71) Applicants reads:
"FONDAZIONE ISTITUTO ITALIANO DI TECNOLOGIA, Genoa (IT); ISTITUTO NAZIONALE PER L' ASSICURAZIONE CONTRO GLI INFORTUNI SUL LAVORO, Rome (IT)"
Should read:
--FONDAZIONE ISTITUTO ITALIANO DI TECNOLOGIA, Genova (IT); ISTITUTO NAZIONALE PER L' ASSICURAZIONE CONTRO GLI INFORTUNI SUL LAVORO, Rome (IT)--

(72) Inventors reads:
"Matteo Latfranchi, Genoa (IT); Stefano D' Angella, Albisola Superiore (IT); Paolo Uboldi, Sant'Olcese (IT); Jody Alessandro Saglia, Genoa (IT); Carlo Sanfilippo, Genoa (IT)"
Should read:
--Matteo Latfranchi, Genova (IT); Stefano D' Angella, Albisola Superiore (Savona) (IT); Paolo Uboldi, Sant'Olcese (Genova) (IT); Jody Alessandro Saglia, Genova (IT); Carlo Sanfilippo, Genova (IT)--

(73) Assignee reads:
"FONDAZIONE ISTITUTO ITALIANO DI TECNOLOGIA, Genoa (IT)"
Should read:
--FONDAZIONE ISTITUTO ITALIANO DI TECNOLOGIA, Genova (IT)--

Signed and Sealed this
Twenty-ninth Day of March, 2022

Drew Hirshfeld
*Performing the Functions and Duties of the
Under Secretary of Commerce for Intellectual Property and
Director of the United States Patent and Trademark Office*